United States Patent [19]
Müller et al.

[11] Patent Number: 6,133,298
[45] Date of Patent: Oct. 17, 2000

[54] FUNGICIDAL MIXTURES

[75] Inventors: Bernd Müller, Frankenthal; Hubert Sauter, Mannheim; Eberhard Ammermann, Heppenheim; Gisela Lorenz, Hambach; Siegfried Strathmann, Limburgerhof; Klaus Schelberger, Gönnheim; Maria Scherer, Landau; Dietrich Mappes, Westheim; Joachim Leyendecker, Landenburg; Herbert Bayer, Mannheim; Ruth Müller, Friedelsheim, all of Germany

[73] Assignee: BASF Aktiengesellschaft, Ludwigshafen, Germany

[21] Appl. No.: 09/171,618

[22] PCT Filed: Apr. 23, 1997

[86] PCT No.: PCT/EP97/02043

§ 371 Date: Oct. 22, 1998

§ 102(e) Date: Oct. 22, 1998

[87] PCT Pub. No.: WO97/40687

PCT Pub. Date: Nov. 6, 1997

[30] Foreign Application Priority Data

Apr. 26, 1996 [DE] Germany .................. 196 16 691
Apr. 29, 1996 [DE] Germany .................. 196 17 071
Sep. 2, 1996 [DE] Germany .................. 196 35 516

[51] Int. Cl.[7] .................. A01N 43/40; A01N 37/18; A01N 37/52; A01N 43/56; A01N 43/64
[52] U.S. Cl. .................. 514/352; 514/383; 514/407; 514/508; 514/538; 514/618; 514/619
[58] Field of Search .................. 514/407, 383, 514/352, 508, 538, 618, 619

[56] References Cited

FOREIGN PATENT DOCUMENTS 0741 970  11/1996  European Pat. Off. .
9521153   8/1995   WIPO .
9601256   1/1996   WIPO .
9601258   1/1996   WIPO .

OTHER PUBLICATIONS

Tomlin; The Pesticide Manual Incorporating The Agrochemicals Handbook, 10$^{th}$ Ed. (1995) pp. 474–475.
Weeds, vol. 15, Jan. 1967, No. 1, 20–22.

*Primary Examiner*—Allen J. Robinson
*Attorney, Agent, or Firm*—Keil & Weinkauf

[57] ABSTRACT

Fungicidal mixtures, comprising a) a carbamate of the formula I

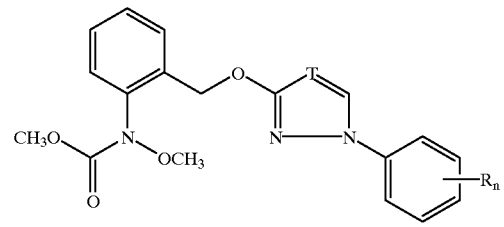

where T is CH or N, n is 0, 1 or 2 and R is halogen, $C_1$—$C_4$—alkyl or $C_1$—$C_4$—haloalkyl, it being possible for the radicals R to be different when n is 2, and/or b) an oxime ether of the formula II

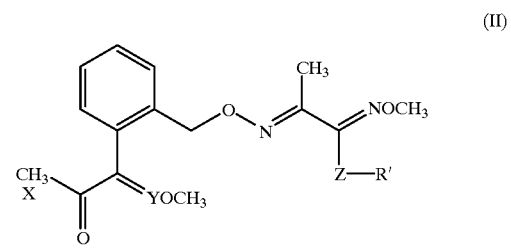

where X is oxygen or amino (NH);

Y is CH or N;

Z is oxygen, sulfur, amino (NH) or $C_1$—$C_4$—alkylamino (N—$C_1$—$C_4$—alkyl);

R' is $C_1$—$C_6$—alkyl, $C_1$—$C_6$—haloalkyl, $C_3$—$C_6$—alkenyl, $C_2$—$C_6$—haloalkenyl, $C_3$—$C_6$—alkynyl, $C_3$—$C_6$—haloalkynyl, ($C_3$—$C_6$—cycloalkyl)methyl, or is benzyl which may be partially or fully halogenated and/or carry one to three of the following radicals: cyano, $C_1$—$C_4$—alkyl, $C_1$—$C_4$—haloalkyl, $C_1$—$C_4$—alkoxy, $C_1$—$C_4$—haloalkoxy and $C_1$—$C_4$—alkylthio;

and c) a dinitroaniline of the formula III

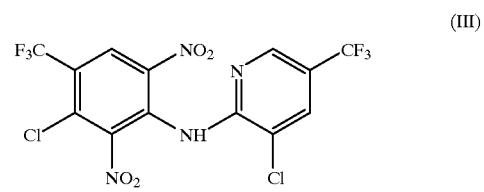

in a synergistically active amount.

15 Claims, No Drawings

FUNGICIDAL MIXTURES

This application is a 371 of PCT/EP97/02043, filed Apr. 23, 1997.

The present invention relates to a fungicidal mixture which comprises a) a carbamate of the formula I

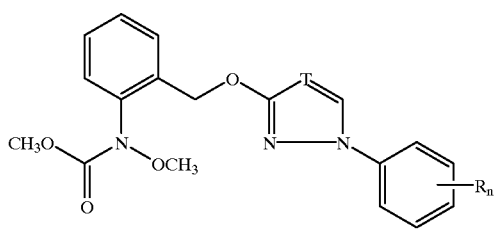

where T is CH or N, n is 0, 1 or 2 and R is halogen, $C_1$—$C_4$-alkyl or $C_1$—$C_4$-haloalkyl, it being possible for the radicals R to be different when n is 2, and/or b) an oxime ether of the formula II

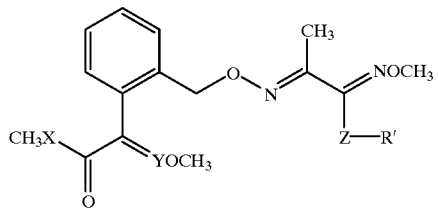

where

X is oxygen or amino (NH);

Y is CH or N;

Z is oxygen, sulfur, amino (NH) or $C_1$—$C_4$-alkylamino (N—$C_1$—$C_4$-alkyl);

R' is $C_1$—$C_6$-alkyl, $C_1$—$C_6$-haloalkyl, $C_3$—$C_6$-alkenyl, $C_2$—$C_6$-haloalkenyl, $C_3$—$C_6$-alkynyl, $C_3$—$C_6$-haloalkynyl, ($C_3$—$C_6$-cycloalkyl)methyl, or is benzyl which may be partially or fully halogenated and/or carry one to three of the following radicals: cyano, $C_1$—$C_4$-alkyl, $C_1$—$C_4$-haloalkyl, $C_1$—$C_4$-alkoxy, $C_1$—$C_4$-haloalkoxy and $C_1$—$C_4$-alkylthio;

and c) a dinitroaniline of the formula III

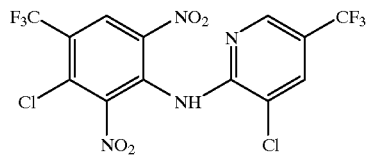

in a synergistically active amount.

Moreover, the invention relates to methods of controlling harmful fungi with mixtures of the compounds I and/or II and III and to the use of the compounds I and/or II and the compound III for the preparation of such mixtures.

The compounds of the formula I, their preparation and their action against harmful fungi have been disclosed in the literature (WO-A 96/01,256 and WO-A 96/01,258).

Compounds of the formula II, their preparation and their action against harmful fungi have been described in WO-A 95/21,153, WO-A 95/21,154 and DE-A 195 28651.0.

The compound III (CAS RN: 79622-59-6, common name: fluazinam;), its preparation and its action against harmful fungi have also been disclosed.

It was an object of the present inventions to provide mixtures which have an improved activity against harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I and/or II and the compound III simultaneously together or separately or by applying the compounds I and/or II and the compound III in succession than when the individual compounds are used.

The present invention covers binary mixtures of the mixtures I and III or II and III and also ternary mixtures of I, II and III.

In particular, the formula I represents carbamates in which the combination of the substituents corresponds to one line of the table which follows:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |

TABLE 1-continued

| No. | T | $R_n$ |
|---|---|---|
| I.46 | CH | 3-CF$_3$ |
| I.47 | CH | 4-CF$_3$ |
| I.48 | CH | 2,4-F$_2$ |
| I.49 | CH | 2,4-Cl$_2$ |
| I.50 | CH | 3,4-Cl$_2$ |
| I.51 | CH | 2-Cl, 4-CH$_3$ |
| I.52 | CH | 3-Cl, 4-CH$_3$ |

The compounds I.12, I.23, I.32 and 1.38 are especially preferred.

The general formula II represents in particular oxime ethers where X is oxygen and Y is CH or X is amino and Y is N.

In addition, preference is given to compounds II where Z is oxygen.

Likewise, preference is given to compounds II where R' is alkyl or benzyl.

With a view to their use in the synergistic mixtures according to the invention, compounds II which are particularly preferred are those listed in the tables below:

TABLE 2

Compounds of the formula IIA where for each compound ZR' corresponds to one row in Table A

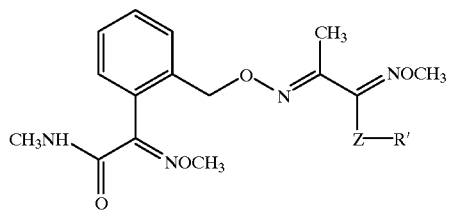

(IIA)

TABLE 3

Compounds of the formula IIB where for each compound ZR' corresponds to one row in Table A

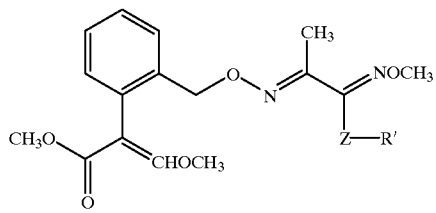

(IIB)

TABLE A

| No. | ZR' |
|---|---|
| II.1 | O—CH$_2$CH$_2$CH$_3$ |
| II.2 | O—CH(CH$_3$)$_2$ |
| II.3 | O—CH$_2$CH$_2$CH$_2$CH$_3$ |
| II.4 | O—CH(CH$_3$)CH$_2$CH$_3$ |
| II.5 | O—CH$_2$CH(CH$_3$)$_2$ |
| II.6 | O—C(CH$_3$)$_3$ |
| II.7 | S—C(CH$_3$)$_3$ |

TABLE A-continued

| No. | ZR' |
|---|---|
| II.8 | O—CH(CH$_3$)CH$_2$CH$_2$CH$_3$ |
| II.9 | O—CH$_2$C(CH$_3$)$_3$ |
| II.10 | O—CH$_2$C(Cl)=CCl$_2$ |
| II.11 | O—CH$_2$CH=CH—Cl (trans) |
| II.12 | O—CH$_2$C(CH$_3$)=CH$_2$ |
| II.13 | O—CH$_2$—(cyclopropyl) |
| II.14 | O—CH$_2$—C$_6$H$_5$ |
| II.15 | O—CH$_2$—[4-F—C$_6$H$_4$] |
| II.16 | O—CH$_2$CH$_3$ |
| II.17 | O—CH(CH$_2$CH$_3$)$_2$ |

In relation to the C=Y double bond, the compounds of the formula II can be present in the E or the Z configuration (in relation to the carboxylic acid function). Accordingly, they can be used in the mixture according to the invention in each case either in the form of a pure E or Z isomers or else in the form of an E/Z isomer mixture. The E/Z isomer mixture or the E isomer is preferably used, the E isomer of compound II being especially preferred.

The C=N double bonds of the oxime ether groups in the side chain of the compounds II can exist in each case in the form of pure E or Z isomers or in the form of E/Z isomer mixtures. The compounds II can be used in the mixtures according to the invention as isomer mixtures or else as pure isomers. With a view to their use, compounds II which are particularly preferred are those where the terminal oxime ether group in the side chain is in the cis configuration (OCH$_3$ group in relation to ZR')

Due to the basic character, the compounds I and II are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I, II and III, with which further active ingredients against harmful fungi or other pests such as insects, arachnids or nematodes, or else herbicidal or growth-regulating active ingredients or fertilizers can be admixed, if so desired.

The mixtures of the compounds I and/or II and III, or the simultaneous joint or separate use of the compounds I and/or II and III, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on curcubits, *Podosphaera leucotricha* on apples, *Puccinia* species on cereals, *Rhizoctonia* species on cotton, rice and lawn, *Ustilago* species on cereals and sugar cane, *Venturia inaequalis* (scab) on apples, *Helminthosporium* species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, *Pseudoperonospora* species on cucurbits and hops, *Plasmopara viticola* on grapevines, *Alternaria* species on vegetables and fruit, and *Fusarium* and *Verticillium* species.

Furthermore, they can be used in the protection of materials (eg. in the protection of wood), for example against *Paecilomyces variotii*.

The compounds I and/or II and III can be applied simultaneously together or separately or in succession, the sequence, in the case of separate application, generally not having any effect on the result of the control measures.

The compounds I and/or II and III are normally used in a weight ratio of from 200:1 to 0.1:1, preferably 100:1 to 1:1, in particular 50:1 to 5:1 (III:I and/or II).

The application rates of the mixtures according to the invention are, in the case of the compounds I and/or II, in general from 0.005 to 0.5 kg/ha, preferably 0.01 to 0.5 kg/ha, in particular 0.01 to 0.3 kg/ha, depending on the nature of the desired effect.

Correspondingly, in the case of the compound III, the application rates are normally from 0.1 to 10 kg/ha, preferably 0.5 to 5 kg/ha, in particular 1 to 4 kg/ha.

For seed treatment, the application rates of the mixture are generally from 0.001 to 100 g/kg seed, preferably 0.01 to 50 g/kg, in particular 0.01 to 10 g/kg.

If phytopathogenic harmful fungi are to be controlled, the separate or joint application of the compounds I and/or II and III or of the mixtures of the compounds I and/or II and III is effected by spraying or dusting the seeds, the plants or the soils before or after sowing of the plants, or before or after plant emergence.

The fungicidal synergistic mixtures according to the invention, or the compounds I and/or II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, ligninsulfite waste liquors or methylcellulose.

Powders, materials for spreading and dusts can be prepared by mixing or jointly grinding the compounds I and/or II and III or the mixture of the compounds I and/or II and III with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I and/or II and III, or of the mixture of the compounds I and/or II and III. The active ingredients are employed in a purity of from 90% to 100%, preferably 95% to 100% (according to NMR spectrum or HPLC.

The compounds I and/or II or III, or the mixtures, or the corresponding formulations, are applied by treating the harmful fungi or the plants, seeds, soils, areas, materials or spaces to be kept free from them with a fungicidally active amount of the mixture, or of the compounds I and/or II and III in the case of separate application. Application can be effected before or after infection by the harmful fungi.

The fungicidal activity of the compounds and of the mixtures is demonstrated by the following experiments:

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The efficacy (W) is calculated as follows using Abbot's formula:

$$W = (1-\alpha) \cdot 100 / \beta$$

α is the fungal infection of the treated plants in % and
β is the fungal infection of the untreated (control) plants in %

An efficacy of 0 means that the infection level of the treated plants corresponds to that of the untreated control plants; an efficacy of 100 means that the treated plants are not infected.

We claim:

1. A fungicidal composition comprising synergistically effective amounts of a) a carbamate I

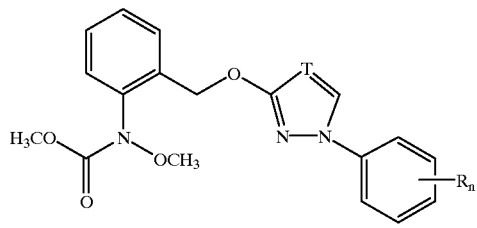

where T is CH or N, n is 0, 1 or 2 and R is halogen, $C_1$—$C_4$-alkyl or $C_1$—$C_4$-haloalkyl, it being possible for the radicals R to be different if n is 2, and c) a dinitroaniline III

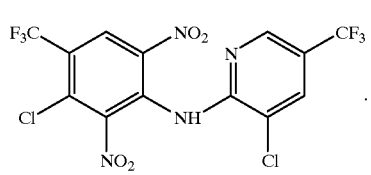

2. The fungicidal composition defined in claim 1 wherein the weight ratio of the dinitroaniline III to the carbamate I is from 200:1 to 0.1:1.

3. The fungicidal composition defined in claim 1, further comprising an oxime ether II

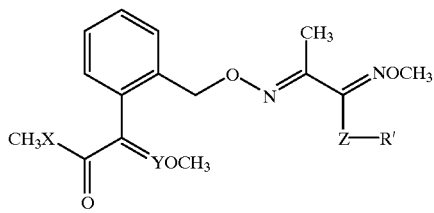

wherein the substituents have the following meaning:

X is oxygen or amino (NH);

Y is CH or N;

Z is oxygen, sulfur, amino (NH) or $C_1$—$C_4$-alkylamino (N—$C_1$—$C_4$-alkyl);

R' is $C_1$—$C_6$-alkyl, $C_1$—$C_6$-haloalkyl, $C_3$—$C_6$-alkenyl, $C_2$—$C_6$-haloalkenyl, $C_3$—$C_6$-alkynyl, $C_3$—$C_6$-haloalkynyl, $C_3$—$C_6$-cycloalkylmethyl, or benzyl which may be partially or fully halogenated and/or may carry one to three of the following radicals: cyano, $C_1$—$C_4$-alkyl, $C_1$—$C_4$-haloalkyl, $C_1$—$C_4$-alkoxy, $C_1$—$C_4$-haloalkoxy and $C_1$—$C_4$-alkylthio.

4. The fungicidal composition defined in claim 3 wherein the weight ratio of the dinitroaniline III to the carbamate I is from 200:1 to 0.1:1.

5. The fungicidal composition defined in claim wherein the weight ratio of the dinitroaniline III to the oxime ether II is from 200:1 to 0.1:1.

6. A method of controlling harmful fungi which comprises treating the harmful fungi, their environment, or plants, seeds, soils, areas, materials or spaces to be kept free from said fungi with synergistically effective amounts of a carbamate I and a dinitroaniline III as set forth in claim 1.

7. The method defined in claim 6, wherein the carbamate I and the dinitroaniline III are applied simultaneously together or separately or in succession.

8. The method defined in claim 6, wherein the carbamate I is applied in an amount of from 0.005 to 0.5 kg/ha.

9. The method defined in claim 6, wherein the dinitroaniline III is applied in an amount of from 0.1 to 10 kg/ha.

10. The method defined in claim 6, further comprising treating the harmful fungi, their environment, or the plants, seeds, soils, areas, materials or spaces to be kept free from said fungi with a synergistically effective amount of an oxime ether II

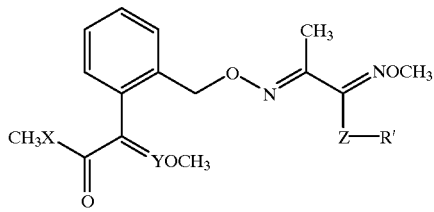

wherein the substituents have the following meaning:

X is oxygen or amino (NH);

Y is CH or N;

Z is oxygen, sulfur, amino (NH) or $C_1$—$C_4$-alkylamino (N—$C_1$—$C_4$-alkyl);

R' is $C_1$—$C_6$-alkyl, $C_1$—$C_6$-haloalkyl, $C_3$—$C_6$-alkenyl, $C_2$—$C_6$-haloalkenyl, $C_3$—$C_6$-alkynyl, $C_3$—$C_6$-haloalkynyl, $C_3$—$C_6$-cycloalkylmethyl, or benzyl which may be partially or fully halogenated and/or may carry one to three of the following radicals: cyano, $C_1$—$C_4$-alkyl, $C_1$—$C_4$-haloalkyl, $C_1$—$C_4$-alkoxy, $C_1$—$C_4$-haloalkoxy and $C_1$—$C_4$-alkylthio.

11. The method defined in claim 10, wherein the carbamate I and the dinitroaniline III are applied simultaneously together or separately or in succession.

12. The method defined in claim 10, wherein the oxime ether II and the dinitroaniline III are applied simultaneously together or separately or in succession.

13. The method defined in claim 10, wherein the carbamate I is applied in an amount of from 0.005 to 0.5 kg/ha.

14. The method defined in claim 10, wherein the oxime ether II is applied in an amount of from 0.005 to 0.5 kg/ha.

15. The method defined in claim 10, wherein the dinitroaniline III is applied in an amount of from 0.1 to 10 kg/ha.

* * * * *

UNITED STATES PATENT AND TRADEMARK OFFICE
CERTIFICATE OF CORRECTION

PATENT NO.: 6,133,298

DATED: October 17, 2000

INVENTOR(S): MUELLER et al.

It is certified that error appears in the above-identified patent and that said Letters Patent is hereby corrected as shown below:

Col. 8, claim 5, line 30, after "claim" insert --3--.

Col. 9, claim 10, line 9, "$C_r$-$C_4$-haloalkoxy" should be --$C_1$-$C_4$-haloalkoxy--.

Signed and Sealed this

Eighth Day of May, 2001

*Attest:*

NICHOLAS P. GODICI

*Attesting Officer*   *Acting Director of the United States Patent and Trademark Office*